US011950760B2

(12) United States Patent
Usuda

(10) Patent No.: US 11,950,760 B2
(45) Date of Patent: Apr. 9, 2024

(54) ENDOSCOPE APPARATUS, ENDOSCOPE OPERATION METHOD, AND PROGRAM

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 739 days.

(21) Appl. No.: 17/078,084

(22) Filed: Oct. 22, 2020

(65) Prior Publication Data
US 2021/0042925 A1    Feb. 11, 2021

Related U.S. Application Data

(63) Continuation of application No. PCT/JP2019/016478, filed on Apr. 17, 2019.

(30) Foreign Application Priority Data

May 17, 2018   (JP) ................. 2018-095391

(51) Int. Cl.
A61B 1/00       (2006.01)
G06T 7/00       (2017.01)

(52) U.S. Cl.
CPC .... A61B 1/000094 (2022.02); A61B 1/00006 (2013.01); A61B 1/0002 (2013.01);
(Continued)

(58) Field of Classification Search
CPC .......... A61B 1/000094; A61B 1/00006; A61B 1/0002; A61B 1/0005; G06T 7/0014;
(Continued)

(56) References Cited

U.S. PATENT DOCUMENTS 8,502,861 B2   8/2013   Hirakawa
8,830,307 B2   9/2014   Hirakawa
(Continued)

FOREIGN PATENT DOCUMENTS

CN   101116608   2/2008
CN   101170940   4/2008
(Continued)

OTHER PUBLICATIONS

"International Search Report (Form PCT/ISA/210) of PCT/JP2019/016478," dated Jul. 23, 2019, with English translation thereof, pp. 1-5.
(Continued)

Primary Examiner — John J Lee
(74) Attorney, Agent, or Firm — JCIPRNET

(57) ABSTRACT

An endoscope apparatus includes: a lesion information acquisition unit that acquires acquired lesion information; a lesion identification unit that compares existing lesion information with the acquired lesion information and determines whether the acquired lesion information corresponds to the same lesion indicated by the existing lesion information; a lesion count unit that counts a lesion count, which is the number of lesions detected in a single endoscopic examination; a display unit; and a control unit that increments the lesion count counted by the lesion count unit by one when the lesion identification unit determines that the acquired lesion information does not correspond to the same lesion indicated by the existing lesion information.

20 Claims, 11 Drawing Sheets

(52) U.S. Cl.
CPC .......... *A61B 1/0005* (2013.01); *G06T 7/0014* (2013.01); *G06T 2207/10016* (2013.01); *G06T 2207/10068* (2013.01); *G06T 2207/20021* (2013.01); *G06T 2207/30096* (2013.01); *G06T 2207/30242* (2013.01)

(58) Field of Classification Search
CPC . G06T 2207/10016; G06T 2207/10068; G06T 2207/20021; G06T 2207/30096; G06T 2207/30242
See application file for complete search history.

(56) References Cited

U.S. PATENT DOCUMENTS

| | | | |
|---|---|---|---|
| 9,186,051 | B2 | 11/2015 | Hirota |
| 9,875,256 | B2 | 1/2018 | Takata et al. |
| 9,898,664 | B2 | 2/2018 | Matsuzaki |
| 10,223,785 | B2 | 3/2019 | Kitamura et al. |
| 11,449,988 | B2 | 9/2022 | Kamon |
| 2005/0171814 | A1 | 8/2005 | Kobayashi et al. |
| 2008/0039692 | A1 | 2/2008 | Hirakawa |
| 2008/0212881 | A1 | 9/2008 | Hirakawa |
| 2008/0303898 | A1 | 12/2008 | Nishimura |
| 2009/0054729 | A1* | 2/2009 | Mori .................... A61B 1/2676 600/114 |
| 2014/0194722 | A1 | 7/2014 | Lee et al. |
| 2016/0360951 | A1* | 12/2016 | Hane .................... A61B 1/0661 |
| 2019/0114738 | A1 | 4/2019 | Sonoda |
| 2019/0231444 | A1* | 8/2019 | Tojo .................... A61B 1/0005 |
| 2020/0184645 | A1 | 6/2020 | Kamon |

FOREIGN PATENT DOCUMENTS

| | | |
|---|---|---|
| CN | 101273916 | 10/2008 |
| CN | 101317749 | 12/2008 |
| CN | 103919573 | 7/2014 |
| CN | 105912831 | 8/2016 |
| CN | 111050628 | 4/2020 |
| JP | 2005165677 | 6/2005 |
| JP | 2008061704 | 3/2008 |
| JP | 2008301968 | 12/2008 |
| JP | 2011024727 | 2/2011 |
| JP | 2012170641 | 9/2012 |
| JP | 2015032127 | 2/2015 |
| JP | 2015173827 | 10/2015 |
| WO | 2006123455 | 11/2006 |
| WO | 2017216922 | 12/2017 |
| WO | 2018069992 | 4/2018 |
| WO | 2019054265 | 3/2019 |

OTHER PUBLICATIONS

"Written Opinion of the International Searching Authority (Form PCT/ISA/237) of PCT/JP2019/016478," dated Jul. 23, 2019, with English translation thereof, pp. 1-12.
"Office Action of Japan Counterpart Application", dated Nov. 9, 2021, with English translation thereof, p. 1-p. 10.
"Office Action of China Counterpart Application", dated Sep. 22, 2023, with English translation thereof, p. 1-p. 19.
"Office Action of Europe Counterpart Application No. 19802615.5", dated Mar. 27, 2023, p. 1-p. 5.
"Office Action of Japan Counterpart Application No. 2020-519528", with English translation thereof, dated Feb. 4, 2022, pp. 1-12.
"Search Report of Europe Counterpart Application No. 19802615.5", dated May 17, 2021, p. 1-p. 9.

* cited by examiner

ENDOSCOPE APPARATUS, ENDOSCOPE OPERATION METHOD, AND PROGRAM

CROSS-REFERENCE TO RELATED APPLICATIONS

This application is a Continuation of PCT International Application No. PCT/JP2019/016478 filed on Apr. 17, 2019, which claims priority under 35 U.S.C. § 119(a) to Japanese Patent Application No. 2018-095391 filed on May 17, 2018. Each of the above application(s) is hereby expressly incorporated by reference, in its entirety, into the present application.

BACKGROUND OF THE INVENTION

1. Field of the Invention

The present invention relates to an endoscope apparatus, an endoscope operation method, and a non-transitory computer readable recording medium storing a program and specifically relates to a technique for counting the number of lesions for which images are captured.

2. Description of the Related Art

In a case where an endoscope is used to make a diagnosis on a patient, the operator (or doctor) needs to observe an image displayed on the monitor of the endoscope apparatus to find a lesion and make a diagnosis while performing complicated operations on the endoscope apparatus. It is desirable to reduce the strain on the operator during the endoscopic examination.

A proposal for assisting an operator in carrying out observation and making a diagnosis during an endoscopic examination has been proposed to date.

For example, a technique described in, for example, JP2015-173827A is intended to preferentially extract an image useful in making a diagnosis from a series of images (endoscopic images) captured by an endoscope apparatus. For example, in the technique described in JP2015-173827A, the number of abnormal regions (lesions) including bleeding, redness, an aphtha, and an ulcer is counted, and a representative image is extracted on the basis of the number of abnormal regions. Then, the extracted representative image is used in the diagnosis.

SUMMARY OF THE INVENTION

In an endoscopic examination, the number of lesions of a patient is essential information. The operator counts the number of lesions during the endoscopic examination and prepares a report on the basis of the number of lesions after the end of the examination.

However, in a case where a large number of lesions are found in a single endoscopic examination or in a case where an endoscopic examination continues over a long time, the operator may fail to accurately count and remember the number of lesions.

In an endoscopic examination, basically, the operator washes out the interior of the body when inserting a scope into the body so as to be ready for observation, and thereafter, carries out detailed observation while withdrawing the scope. The scope travels the same route and back at the time of insertion and at the time of withdrawal, and therefore, the operator should find the same number of lesions at the time of insertion and at the time of withdrawal. However, in an actual endoscopic examination, at the time of withdrawal, the operator may overlook a lesion found at the time of insertion because of various factors.

To address such a problem, it is desirable to assist the operator in performing the endoscopic examination by accurately counting the number of lesions during the endoscopic examination period to thereby reduce the strain on the operator.

JP2015-173827A does not mention a technique in which the number of lesions of a patient is accurately counted during the endoscopic examination period to assist the operator in performing the endoscopic examination.

The present invention has been made in view of the above-described circumstances, and an object thereof is to provide an endoscope apparatus, an endoscope operation method, and a program with which the strain on the operator can be reduced and the endoscopic examination can be performed accurately and efficiently by accurately counting the number of lesions during the endoscopic examination period so as to assist the operator.

An endoscope apparatus, which is an aspect of the present invention for achieving the above-described object, includes: a lesion information acquisition unit that acquires, in a case where a lesion is detected from time-series images captured during an endoscopic examination period, acquired lesion information that indicates at least one of a first lesion image representing the detected lesion or a feature value indicating a feature of the first lesion image; a lesion identification unit that compares existing lesion information, which is lesion information previously acquired by the lesion information acquisition unit, with the acquired lesion information newly acquired by the lesion information acquisition unit and determines whether the newly acquired lesion information corresponds to the same lesion indicated by the existing lesion information; a lesion count unit that counts a lesion count, which is the number of lesions detected in a single endoscopic examination; a display unit that displays the lesion count counted by the lesion count unit; and a control unit that controls the lesion count unit and increments the lesion count counted by the lesion count unit by one when the lesion identification unit determines that the newly acquired lesion information does not correspond to the same lesion indicated by the existing lesion information.

According to this aspect, the lesion count, which is the number of lesions detected in a single endoscopic examination, is counted, and the counted lesion count is displayed on the display unit. Therefore, the strain on the operator performing an endoscopic examination can be reduced, and the endoscopic examination can be performed accurately and efficiently.

Preferably, the endoscope apparatus further includes an examination division unit that outputs to the control unit a division instruction for dividing the endoscopic examination into a first examination and a second examination, and the control unit causes the lesion count unit to count a lesion count in the first examination and a lesion count in the second examination separately on the basis of the division instruction.

According to this aspect, the examination division unit outputs to the control unit a division instruction for dividing the endoscopic examination into a first examination and a second examination, and the control unit causes the lesion count unit to count the lesion count in the first examination and the lesion count in the second examination separately on the basis of the division instruction. Accordingly, the lesion count can be counted separately in a single endoscopic examination, and the operator can be assisted more appropriately.

Preferably, in the division instruction output by the examination division unit, the first examination is an examination that is performed at the time of insertion of a scope, and the second examination is an examination that is performed at the time of withdrawal of the scope.

According to this aspect, the endoscopic examination is divided in to an examination that is performed at the time of insertion of the scope and an examination that is performed at the time of withdrawal of the scope, and the lesion count is counted. Therefore, the operator can perform the examination while comparing the number of lesions found at the time of insertion and the number of lesions found at the time of withdrawal, and the strain on the operator at the time of examination can be reduced. For example, the operator performs an endoscopic examination while comparing the number of lesions found at the time of insertion and the number of lesions found at the time of withdrawal to thereby reduce the possibility of overlooking a lesion at the time of endoscopic examination.

An endoscope apparatus, which is an aspect of the present invention for achieving the above-described object, includes: a lesion information acquisition unit that acquires, in a case where a lesion is detected from time-series images captured during an endoscopic examination period, acquired lesion information that indicates at least one of a first lesion image representing the detected lesion or a feature value indicating a feature of the first lesion image; a lesion identification unit that identifies a lesion from the time-series images; a lesion count unit that counts a lesion count, which is the number of lesions detected in a single endoscopic examination; a display unit that displays the lesion count counted by the lesion count unit; a control unit that controls the lesion count unit; and an examination division unit that outputs to the control unit a division instruction for dividing the endoscopic examination into a first examination that is performed at the time of insertion of a scope and a second examination that is performed at the time of withdrawal of the scope. In the first examination, the lesion identification unit compares existing lesion information, which is the acquired lesion information previously acquired by the lesion information acquisition unit, with the acquired lesion information newly acquired by the lesion information acquisition unit and determines whether the newly acquired lesion information indicates the same lesion indicated by the existing lesion information, and the control unit increments the lesion count counted by the lesion count unit by one when the lesion identification unit determines that the newly acquired lesion information does not indicate the same lesion indicated by the existing lesion information. In the second examination that follows the first examination, the lesion identification unit compares the existing lesion information previously acquired in the first examination with the acquired lesion information newly acquired in the second examination and determines whether the newly acquired lesion information indicates the same lesion indicated by the existing lesion information previously acquired in the first examination, the control unit decrements a remaining lesion count by one to update the remaining lesion count, the remaining lesion count being the lesion count when the first examination is completed, in a case where the lesion identification unit determines that the newly acquired lesion information indicates the same lesion indicated by the existing lesion information previously acquired in the first examination, and the display unit displays the remaining lesion count on the basis of the remaining lesion count.

According to this aspect, the remaining lesion count is updated and the remaining lesion count is displayed on the display unit, and therefore, the operator can be assisted appropriately in performing the examination. For example, the operator performs an endoscopic examination while checking the remaining lesion count to thereby reduce the possibility of overlooking a lesion at the time of the endoscopic examination.

Preferably, in a case where the lesion identification determines that the newly acquired lesion information does not indicate the same lesion indicated by the existing lesion information in the first examination, the control unit causes the lesion count unit to do a count as a new lesion count in the second examination, and the display unit displays the new lesion count.

According to this aspect, a lesion newly found in the second examination is counted as a new lesion count, and the new lesion count is displayed on the display unit. Therefore, the operator can be assisted in performing an examination more appropriately.

Preferably, the examination division unit outputs the division instruction to the control unit on the basis of a user instruction.

According to this aspect, the division instruction is output to the control unit on the basis of a user instruction, and therefore, the user (for example, the operator) can divide the examination at a desired timing.

Preferably, the examination division unit automatically outputs the division instruction to the control unit.

According to this aspect, the division instruction is automatically output to the control unit, and therefore, the strain on the operator can be reduced.

Preferably, the display unit displays the lesion count together with an image showing the endoscopic examination that is ongoing.

According to this aspect, the lesion count is displayed on the display unit together with an image showing the endoscopic examination that is ongoing, and therefore, the operator can check the lesion count while carrying out the observation.

Preferably, in the endoscope apparatus, the existing lesion information has a second lesion image corresponding to the first lesion image, and the display unit displays the lesion count together with the second lesion image.

According to this aspect, the lesion count is displayed on the display unit together with the second lesion image, and therefore, the operator can check the previously acquired lesion image and the lesion count simultaneously.

Preferably, in a case where the examination division unit outputs the division instruction to the control unit, the display unit displays the lesion count in the first examination and the lesion count in the second examination.

According to this aspect, in a case where the examination division unit outputs the division instruction to the control unit, the lesion count in the first examination and the lesion count in the second examination are displayed. Therefore, the operator can be assisted appropriately.

Preferably, the endoscope apparatus further includes a saving unit that saves the existing lesion information, and the lesion identification unit compares the existing lesion information saved in the saving unit with the acquired lesion information newly acquired by the lesion information acquisition unit and determines whether the newly acquired lesion information corresponds to the same lesion indicated by the existing lesion information.

Preferably, the saving unit saves all or some of pieces of acquired lesion information acquired by the lesion information acquisition unit as pieces of existing lesion information.

According to this aspect, all or some of the pieces of acquired lesion information acquired by the lesion information acquisition unit are saved as pieces of existing lesion information, and therefore, the pieces of existing lesion information can be saved efficiently.

An endoscope operation method, which is another aspect of the present invention, includes: a lesion image acquisition step of acquiring, in a case where a lesion is detected from time-series images captured during an endoscopic examination period, acquired lesion information that indicates at least one of a first lesion image representing the detected lesion or a feature value indicating a feature of the first lesion image; a lesion identification step of comparing existing lesion information, which is first lesion information previously acquired in the lesion image acquisition step, with the acquired lesion information newly acquired in the lesion image acquisition step and determining whether the newly acquired lesion information corresponds to the same lesion indicated by the existing lesion information; a lesion count step of counting a lesion count, which is the number of lesions detected in a single endoscopic examination; a display step of displaying the lesion count counted in the lesion count step; and a control step of controlling the lesion count step and incrementing the lesion count counted in the lesion count step by one when the lesion identification step determines that the newly acquired lesion information does not correspond to the same lesion indicated by the existing lesion information.

A program, which is yet another aspect of the present invention, causes a computer to perform an endoscope operation process including: a lesion image acquisition step of acquiring, in a case where a lesion is detected from time-series images captured during an endoscopic examination period, acquired lesion information that indicates at least one of a first lesion image representing the detected lesion or a feature value indicating a feature of the first lesion image; a lesion identification step of comparing existing lesion information, which is first lesion information previously acquired in the lesion image acquisition step, with the acquired lesion information newly acquired in the lesion image acquisition step and determining whether the newly acquired lesion information corresponds to the same lesion indicated by the existing lesion information; a lesion count step of counting a lesion count, which is the number of lesions detected in a single endoscopic examination; a display step of displaying the lesion count counted in the lesion count step; and a control step of controlling the lesion count step and incrementing the lesion count counted in the lesion count step by one when the lesion identification step determines that the newly acquired lesion information does not correspond to the same lesion indicated by the existing lesion information.

According to the present invention, the lesion count, which is the number of lesions detected in a single endoscopic examination, is counted, and the counted lesion count is displayed on the display unit. Therefore, the strain on the operator performing an endoscopic examination can be reduced, and the endoscopic examination can be performed accurately and efficiently.

DESCRIPTION OF THE PREFERRED EMBODIMENTS

Hereinafter, preferred embodiments of an endoscope apparatus, an endoscope operation method, and a program according to the present invention will be described with reference to the attached drawings.

Figure 1:
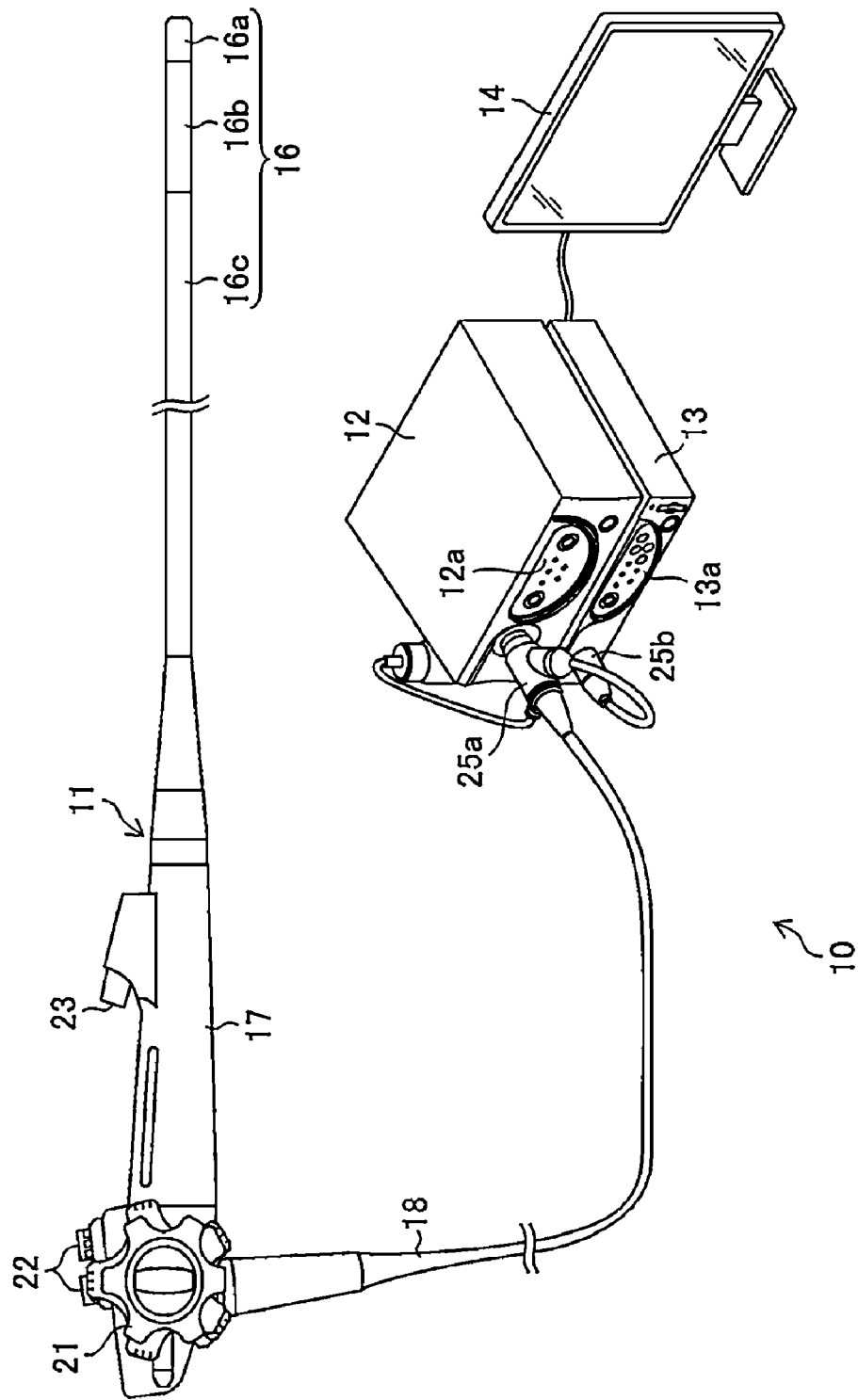
FIG. 1 is an external perspective view of an endoscope apparatus.

FIG. 1 is an external perspective view of an endoscope apparatus 10.

As illustrated in FIG. 1, the endoscope apparatus 10 includes, as its major units, an endoscope (here, a soft endoscope) 11 that captures images of an observation target in a subject, a light source device 12, a processor device 13, and a display 14, which is, for example, a liquid crystal monitor.

The light source device 12 supplies to the endoscope 11 various types of illumination light including white light for capturing a normal image and light in a specific wavelength range for capturing a special-light image.

The processor device 13 is a device that can also function as one form of the endoscope apparatus 10 and has a function of generating image data of a normal image and/or a special-light image for display or recording on the basis of an image signal acquired by the endoscope 11.

The display 14 displays, for example, a normal image or a special-light image on the basis of image data for display input from the processor device 13.

The endoscope 11 includes an insertion part 16 that is flexible and inserted into the subject, a handheld operation part 17 that is coupled to the proximal end part of the insertion part 16, is a grip for holding the endoscope 11, and is used to operate the insertion part 16, and a universal cord 18 that connects the handheld operation part 17 to the light source device 12 and to the processor device 13.

Figure 2:
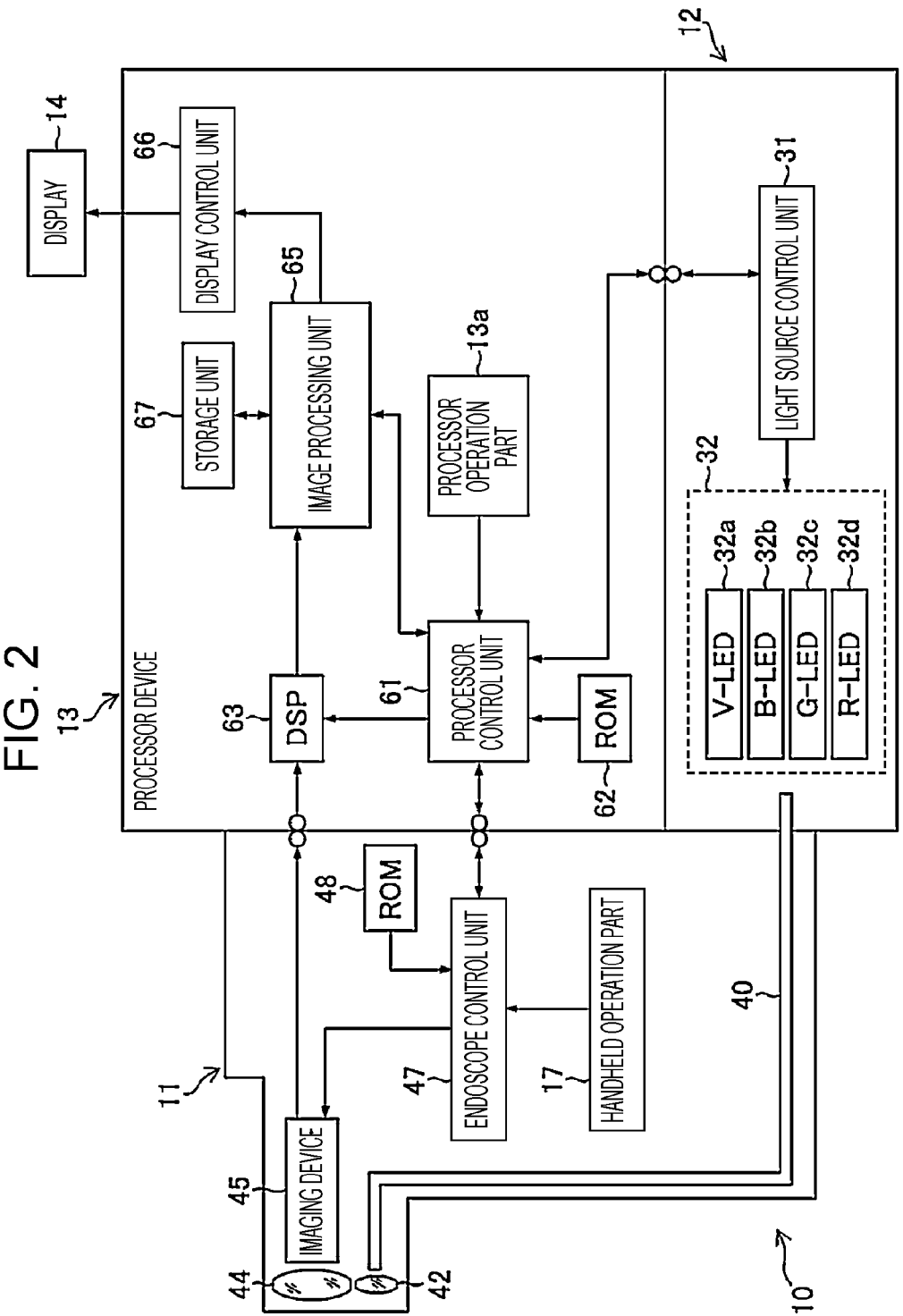
FIG. 2 is a block diagram illustrating an electric configuration of the endoscope apparatus.

In an insertion part tip part 16a, which is the tip part of the insertion part 16, for example, an illumination lens 42, an object lens 44, and an imaging device 45 are built (see FIG. 2). At the rear end of the insertion part tip part 16a, a bending part 16b that is bendable is coupled. At the rear end of the bending part 16b, a flexible pipe part 16c having flexibility is coupled. The insertion part tip part 16a and the bending part 16b constitute the scope head.

On the handheld operation part 17, for example, an angle knob 21, an operation button 22, and a forceps port 23 are provided. The angle knob 21 is rotated and operated to adjust the bending direction and the amount of bending of the bending part 16b. The operation button 22 is used to perform various operations including air supply, water supply, and suction. The forceps port 23 communicates with a forceps channel in the insertion part 16. Note that as the angle knob 21, an up-down angle knob for moving the bending part 16b upward and downward and a right-left angle knob for moving the bending part 16b rightward and leftward are provided.

In the universal cord 18, for example, an air-supply and/or water-supply channel, a signal cable, and a light guide 40 are incorporated. At the tip part of the universal cord 18, a connector part 25a that is connected to the light source device 12 and a connector part 25b that is connected to the processor device 13 are provided. Accordingly, illumination light is supplied to the endoscope 11 from the light source device 12 via the connector part 25a, and an image signal acquired by the endoscope 11 is input to the processor device 13 via the connector part 25b.

Note that on the light source device 12, a light source operation part 12a including, for example, a power button, a turn-on button for turning on the light source, and a brightness adjusting button is provided. On the processor device 13, a processor operation part 13a including a power button and an input unit that accepts input from a pointing device, such as a mouse, not illustrated is provided.

FIG. 2 is a block diagram illustrating an electrical configuration of the endoscope apparatus 10.

As illustrated in FIG. 2, the endoscope 11 has, as its major units, the light guide 40, the illumination lens 42, the object lens 44, the imaging device 45, the handheld operation part 17, an endoscope control unit 47, and a ROM (read-only memory) 48.

As the light guide 40, for example, a large-diameter optical fiber or a fiber bundle is used. The entry end of the light guide 40 is inserted in the light source device 12 via the connector part 25a, and the exit end thereof passes through the insertion part 16 so as to face the illumination lens 42 provided in the insertion part tip part 16a. Illumination light supplied from the light source device 12 to the light guide 40 passes through the illumination lens 42 to irradiate an observation target. The illumination light is reflected and/or scattered at the observation target and enters the object lens 44.

The object lens 44 forms an image of the entering reflected light or scattered light resulting from the illumination light (that is, an optical image of the observation target) on the imaging surface of the imaging device 45.

The imaging device 45 is an imaging device of the CMOS (complementary metal-oxide semiconductor) type or the CCD (charge-coupled device) type and is positioned and fixed relative to the object lens 44 at a position on the further side than the object lens 44. On the imaging surface of the imaging device 45, a plurality of pixels formed of a plurality of photoelectric conversion elements (photodiodes) that photoelectrically convert the optical image are arranged in two dimensions. On the entry surface side of the plurality of pixels of the imaging device 45 in this example, a color filter of red (R), green (G), or blue (B) is arranged for each pixel to thereby form R pixels, G pixels, and B pixels. Note that the filter arrangement of the R, G, and B filters is typically based on the Bayer pattern but is not limited to this.

The imaging device 45 converts the optical image formed by the object lens 44 to an electric image signal and outputs the image signal to the processor device 13.

Note that in a case where the imaging device 45 is of the CMOS type, an A/D (analog/digital) converter is built therein, and a digital image signal is directly output from the imaging device 45 to the processor device 13. In a case where the imaging device 45 is of the CCD type, the image signal output from the imaging device 45 is converted to a digital image signal by, for example, an A/D converter not illustrated, and thereafter, the digital image signal is output to the processor device 13.

The handheld operation part 17 has a still-image capture button and an image capture mode setting unit for setting a normal-image capture mode and a special-light image capture mode.

The endoscope control unit 47 reads from, for example, the ROM 48 various programs and data and successively executes the programs in response to an operation on the handheld operation part 17 to mainly control driving of the imaging device 45. For example, in the normal-image capture mode, the endoscope control unit 47 controls the imaging device 45 so as to read signals from the R pixels, G pixels, and B pixels of the imaging device 45. In the special-light image capture mode and in a case where violet light is emitted from a V-LED 32a as illumination light or in a case where blue light is emitted from a B-LED 32b as illumination light in order to acquire a special-light image, the endoscope control unit 47 controls the imaging device 45 so as to only read signals from the B pixels of the imaging device 45 having spectral sensitivity in the wavelength ranges of the violet light and the blue light.

The endoscope control unit 47 communicates with a processor control unit 61 of the processor device 13 to transmit to the processor device 13, for example, input operation information input at the handheld operation part 17 and identification information for identifying the type of the endoscope 11 stored in the ROM 48.

The light source device 12 has a light source control unit 31 and a light source unit 32. The light source control unit 31 controls the light source unit 32 and communicates with the processor control unit 61 of the processor device 13 to exchange various types of information.

The light source unit 32 has, for example, a plurality of semiconductor light sources. In this embodiment, the light source unit 32 has LEDs of four colors, namely, the V-LED (Violet Light Emitting Diode) 32a, the B-LED (Blue Light Emitting Diode) 32b, a G-LED (Green Light Emitting Diode) 32c, and an R-LED (Red Light Emitting Diode) 32d. The V-LED 32a is a violet light source that emits violet light in a wavelength range from 380 to 420 nm and has a center wavelength of 405 nm. The B-LED 32b is a blue semiconductor light source that emits blue light in a wavelength range from 420 to 500 nm and has a center wavelength of 460 nm. The G-LED 32c is a green semiconductor light source that emits green light in a wavelength range from 480 to 600 nm. The R-LED 32d is a red semiconductor light source that emits red light in a wavelength range from 600 to 650 nm and has a center wavelength of 620 to 630 nm. Note that the center wavelengths of the V-LED 32a and the B-LED 32b have a width of about ±5 nm to ±10 nm.

The light source control unit 31 can separately control, for example, tuning on and off of the LEDs 32a to 32d and the amounts of light emission thereof during turning on, by inputting control signals independent of each other to the respective LEDs. In the normal-image capture mode, the light source control unit 31 turns on all of the V-LED 32a, the B-LED 32b, the G-LED 32c, and the R-LED 32d. Accordingly, in the normal-image capture mode, white light including violet light, blue light, green light, and red light is used as the illumination light.

On the other hand, in the special-light image capture mode, the light source control unit 31 turns on one light source among the V-LED 32a, the B-LED 32b, the G-LED 32c, and the R-LED 32d or a plurality of light sources obtained by combining some of the LEDs as appropriate. In a case where the light source control unit 31 turns on a plurality of light sources, the light source control unit 31 controls the amounts of light emission of the respective light sources (light amount ratio) to thereby enable capturing of images of a plurality of layers at different depths in the subject.

Light rays in the respective colors emitted from the LEDs 32a to 32d pass through an optical path coupling part formed of, for example, a mirror or a lens and a diaphragm mechanism (not illustrated) and enter the light guide 40 inserted in the endoscope 11.

Note that as the illumination light of the light source device 12, light in various wavelength ranges suitable for the observation, that is, for example, white light (light in the wavelength range of white or light in a plurality of wavelength ranges), light in one or more specific wavelength ranges (special light), or a combination thereof, is selected. The specific wavelength range of the special light is a range narrower than the wavelength range of white.

A first example of the specific wavelength range is, for example, the blue range or the green range in the visible range. The wavelength range of the first example includes a wavelength range of 390 nm or more and 450 nm or less or 530 nm or more and 550 nm or less, and light of the first example has its peak wavelength in a wavelength range of 390 nm or more and 450 nm or less or 530 nm or more and 550 nm or less.

A second example of the specific wavelength range is, for example, the red range in the visible range. The wavelength range of the second example includes a wavelength range of 585 nm or more and 615 nm or less or 610 nm or more and 730 nm or less, and light of the second example has its peak wavelength in a wavelength range of 585 nm or more and 615 nm or less or 610 nm or more and 730 nm or less.

A third example of the specific wavelength range includes a wavelength range in which the light absorption coefficient differs between oxyhemoglobin and reduced hemoglobin, and light of the third example has its peak wavelength in a wavelength range in which the light absorption coefficient differs between oxyhemoglobin and reduced hemoglobin. The wavelength range of the third example includes a wavelength range of $400\pm10$ nm, $440\pm10$ nm, $470\pm10$ nm, or 600 nm or more and 750 nm or less, and light of the third example has its peak wavelength in a wavelength range of $400\pm10$ nm, $440\pm10$ nm, $470\pm10$ nm, or 600 nm or more and 750 nm or less described above.

A fourth example of the specific wavelength range is the wavelength range (from 390 nm to 470 nm) of excitation light that is used in observation (fluorescence observation) of fluorescence emitted from a fluorescent substance in the living body and that excites the fluorescent substance.

A fifth example of the specific wavelength range is the wavelength range of infrared light. The wavelength range of the fifth example includes a wavelength range of 790 nm or more and 820 nm or less or 905 nm or more and 970 nm or less, and light of the fifth example has its peak wavelength in a wavelength range of 790 nm or more and 820 nm or less or 905 nm or more and 970 nm or less.

The processor device 13 has, for example, the processor operation part 13a, the processor control unit 61, a ROM 62, a digital signal processing circuit (DSP: Digital Signal Processor) 63, an image processing unit 65, a display control unit 66, and a storage unit 67.

The processor operation part 13a includes, for example, the power button and the input unit that accepts input of, for example, a coordinate position that is specified on the display 14 with the mouse and a click (instruction for execution).

The processor control unit 61 reads from the ROM 62 necessary programs and data and successively performs processes in accordance with input operation information input at the processor operation part 13a and input operation information input at the handheld operation part 17 and received via the endoscope control unit 47 to thereby control the units of the processor device 13 and control the light source device 12. Note that the processor control unit 61 may accept necessary instructions input from another external device, such as a keyboard, connected via an interface not illustrated.

The DSP 63, which functions as one form of an image acquisition unit that acquires pieces of image data of frames of a moving image output from the endoscope 11 (imaging device 45), performs in accordance with control by the processor control unit 61, various types of signal processing including, for example, defect correction, offsetting, white balance correction, gamma correction, and demosaicing for image data of one frame of the moving image input from the endoscope 11 to generate image data of the one frame.

The image processing unit 65 receives image data from the DSP 63 and preforms image processing including, for example, color conversion, color enhancement, and structural enhancement for the received image data as necessary to generate image data representing an endoscopic image in which the observation target is present. The color conversion is a process for converting colors by performing, for example, a 3×3 matrix process, gradation transformation, and a three-dimensional look-up table process for the image data. The color enhancement is a process for enhancing colors for the image data subjected to the color conversion such that, for example, the tint of blood vessels and that of a mucous membrane are made different. The structural enhancement is a process for enhancing a specific tissue or structure included in the observation target, which is, for example, a blood vessel or a pit pattern, and is performed for the image data subjected to the color enhancement.

In response to an image capture instruction for a still image or a moving image, pieces of image data of the respective frames of the moving image processed by the image processing unit 65 are recorded to the storage unit 67 as the still image or the moving image for which the image capture instruction has been given.

The display control unit 66 generates from received image data, display data for displaying a normal image or a special-light image on the display 14 and outputs the generated display data to the display 14 to display a display image on the display 14.

First Embodiment

Figure 3:
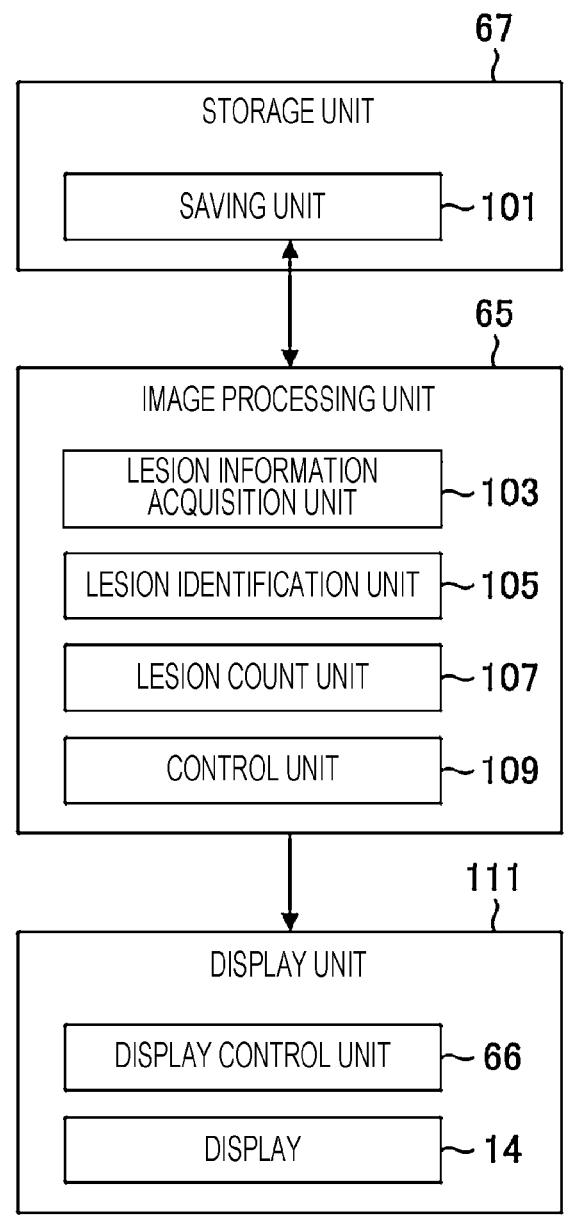
FIG. 3 is a block diagram illustrating the major functions of the endoscope apparatus.

FIG. 3 is a block diagram illustrating the major functions of the endoscope apparatus 10 according to the present invention.

A saving unit 101 is provided in the storage unit 67, and a lesion information acquisition unit 103, a lesion identification unit 105, a lesion count unit 107, and a control unit 109 are provided in the image processing unit 65. A display unit 111 is formed of the display control unit 66 and the display 14.

The lesion information acquisition unit 103 acquires, in a case where a lesion is detected from time-series images captured during an endoscopic examination period, acquired lesion information about the detected lesion. Here, first lesion information is information indicating at least one of a first lesion image that represents the detected lesion or a feature value that indicates the features of the first lesion image. A lesion image representing a lesion is an image of the lesion or an image including an image of the lesion. As a feature value indicating the features of a lesion image, various parameters indicating the feature value of the image can be used. Note that a publicly known technique is applied to the feature value, and therefore, a detailed description thereof is omitted. Here, an endoscopic examination period means the period of a single endoscopic examination for a single examinee.

Figure 4:
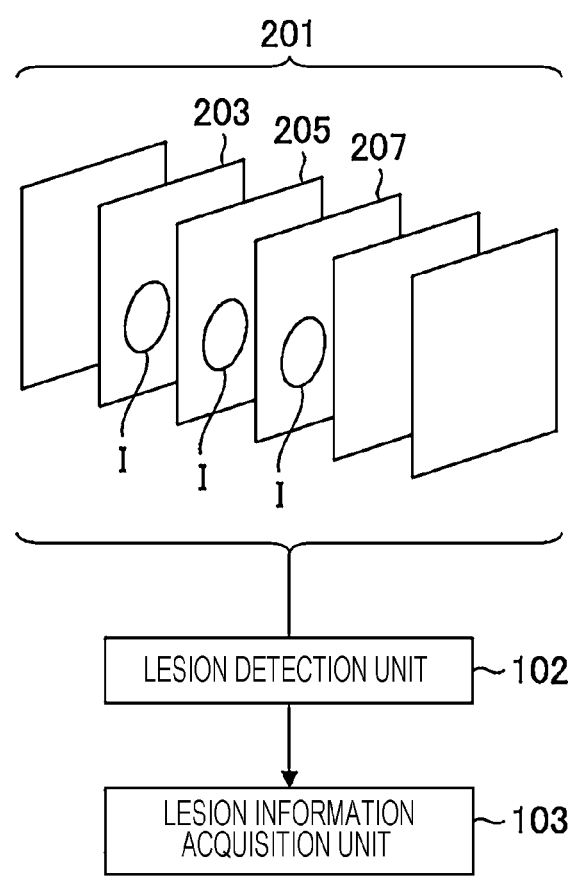
FIG. 4 is a diagram illustrating an example where acquired lesion information is acquired.

FIG. 4 is a diagram illustrating an example where the lesion information acquisition unit 103 acquires acquired lesion information. In this example, a plurality of time-series images (moving image) 201 captured by the endoscope 11 are input to the image processing unit 65 during an endoscopic examination period. The moving image is formed of a plurality of frames, and some of the frames have a lesion I. In this example, a frame 203, a frame 205, and a frame 207 have the lesion I (an image of the lesion I).

In the image processing unit 65, a lesion detection unit 102 is provided. When the plurality of images 201 are input to the lesion detection unit 102, the frame 203, the frame 205, and the frame 207 having the lesion I are extracted. Note that detection of a lesion by the lesion detection unit 102 is performed by using a publicly known technique, and therefore, a detailed description thereof is omitted here. A lesion image having the lesion I detected by the lesion detection unit 102 is input to the lesion information acquisition unit 103. The lesion information acquisition unit 103 acquires acquired lesion information indicating the lesion I.

Figure 5:
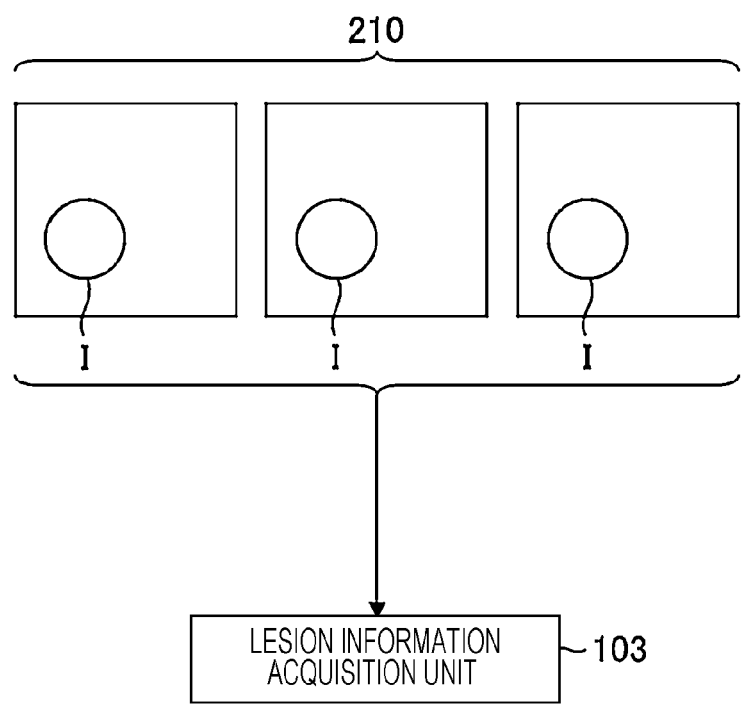
FIG. 5 is a diagram illustrating another example where acquired lesion information is acquired.

FIG. 5 is a diagram illustrating another example where the lesion information acquisition unit 103 acquires acquired lesion information. In this example, a plurality of time-series images (still images) 210 captured by the operator using the endoscope 11 are input to the image processing unit 65 during an endoscopic examination period. The operator finds the lesion I while performing the endoscopic examination, and a single image or a plurality of images of the lesion I are acquired by the endoscope 11. The acquired images 210 are input to the lesion information acquisition unit 103.

Referring back to FIG. 3, the saving unit 101 saves existing lesion information. Here, existing lesion information is acquired lesion information that was previously acquired. That is, existing lesion information is acquired lesion information that was acquired in the past. The saving unit 101 saves all of the pieces of acquired lesion information or some of the pieces of acquired lesion information acquired by the lesion information acquisition unit 103 as pieces of existing lesion information. In the saving unit 101, at least one of a second lesion image or a feature value indicating the features of the second lesion image is saved as existing lesion information. Although the saving unit 101 is provided in the storage unit 67, a case where existing lesion information is retained in, for example, a memory (a RAM (random access memory) not illustrated of the processor control unit 61) is also assumed to be the state where existing lesion information is saved.

In a case where some of the pieces of acquired lesion information are saved in the saving unit 101, for example, the latest one piece of acquired lesion information newly acquired by the lesion information acquisition unit 103 is saved. The saving unit 101 may save representative information selected from among the pieces of acquired lesion information on the basis of a predetermined criterion. For example, representative information is information, for each lesion, that can indicate the lesion most appropriately. Further, the saving unit 101 may save existing lesion information when the environment (the light source, enlargement ratio, or composition) for capturing an image of a lesion changes.

The lesion identification unit 105 compares existing lesion information, which is first lesion information previously acquired by the lesion information acquisition unit 103, with acquired lesion information newly acquired by the lesion information acquisition unit 103. The lesion identification unit 105 determines whether the newly acquired lesion information indicates the same lesion indicated by the existing lesion information. The lesion identification unit 105 compares, for example, the first lesion image with the second lesion image. In this case, the lesion identification unit 105 is formed of a determiner that determines where the two images, namely, the first lesion image and the second lesion image, represent the same lesion. The lesion identification unit 105 may compare the feature value that indicates the features of the first lesion image with the feature value that indicates the features of the second lesion image. In this case, the lesion identification unit 105 extracts a feature vector corresponding to the first lesion image and a feature vector corresponding to the second lesion image and determines whether the acquired lesion information and the existing lesion information indicate the same lesion on the basis of whether the degree of similarity between the feature vectors is equal to or higher than a threshold value. Here, examples of the feature vector include a histogram of the image, a BoVW (Bag of Visual Words) vector, and a feature vector based on a neural network.

A comparison by the lesion identification unit 105 may be made for all pieces of existing lesion information saved in the saving unit 101 or for some of the pieces of existing lesion information. In identification performed by the lesion identification unit 105, information that is input in relation to the first lesion image and the second lesion image may be used. The information input in relation to the first lesion image and the second lesion image includes, for example, the examination time, frame number, scope position, and lesion type. For example, the lesion identification unit 105 compares acquired lesion information with existing lesion information for which the examination time is close to that of the acquired lesion information.

The lesion count unit 107 counts and retains a lesion count, which is the number of lesions detected in a single endoscopic examination. Counting of the lesion count by the lesion count unit 107 is controlled by the control unit 109. Note that the initial value of the lesion count of the lesion count unit 107 is equal to 0, and the lesion count is set to the initial value (lesion count=0) at the start of an endoscopic examination.

The control unit 109 controls the lesion count unit 107 on the basis of the result of identification by the lesion identification unit 105. When the lesion identification unit 105 determines that acquired lesion information and existing lesion information indicate the same lesion, the control unit 109 maintains the lesion count counted by the lesion count unit 107. That is, the control unit 109 controls counting such that the lesion count unit 107 does not count the same lesion in a duplicated manner.

The display unit 111 displays the lesion count counted by the lesion count unit 107. In the display unit 111, the lesion count is displayed on the display 14 in accordance with control by the display control unit 66. The display form of the display unit 111 will be described in detail below.

Figure 6:
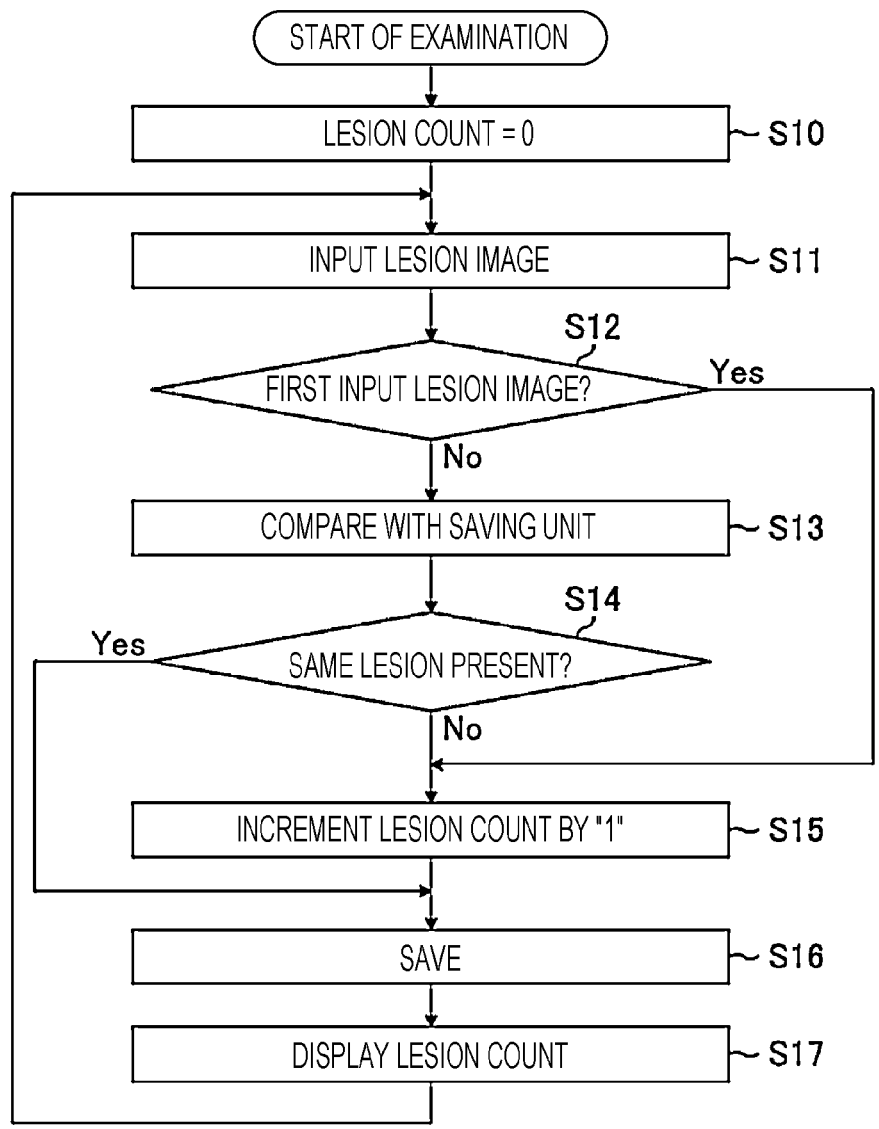
FIG. 6 is a flowchart illustrating operations by the endoscope apparatus.

Now, the process of operations by the endoscope apparatus 10 (corresponding to the endoscope operation method of the present invention) are described. FIG. 6 is a flowchart illustrating the operations by the endoscope apparatus 10. Note that a case where a first lesion image and a second lesion image are input as acquired lesion information and existing lesion information respectively is described below.

An endoscopic examination is started, and the lesion count unit 107 sets the lesion count to the initial value (lesion count=0) (step S10). Thereafter, a first lesion image, which is acquired lesion information, is input to the lesion information acquisition unit 103 (step S11: lesion image acquisition step). The control unit 109 determines whether the first lesion image is a first lesion image (acquired lesion information) that is input first after the start of the endoscopic examination (step S12) and sets the lesion count retained by the lesion count unit 107 to 1 (step S15). Further, the first lesion image input first is saved in the saving unit 101 (step S16). The display unit 111 displays the lesion count "1" (step S17).

On the other hand, in a case where the control unit 109 determines that the first lesion image is not a first lesion image (acquired lesion information) that is input first, the lesion identification unit 105 compares the first lesion image with second lesion images saved in the saving unit 101 (step S13: lesion identification step). In a case where the lesion identification unit 105 determines that a second lesion image that represents the same lesion is present in the saving unit 101 (step S14), the first lesion image is saved in the saving unit 101 (step S16). In this case, the lesion count retained by the lesion count unit 107 is maintained and retained. The display unit 111 displays the lesion count (step S17). On the other hand, in a case where the lesion identification unit 105 determines that the same lesion is not present in the saving unit 101 (step S14), the control unit 109 increments the lesion count by one (step S15: control step and count step). The first lesion image is saved in the saving unit 101 (step S16), and the incremented lesion count is displayed on the display unit 111 (step S17: display step).

In the above-described embodiment, the hardware configuration of the processing units that perform various types of processing is implemented as various processors as described below. The various processors include a CPU (central processing unit), which is a general-purpose processor executing software (program) to function as various processing units, a programmable logic device (PLD), such as an FPGA (field-programmable gate array), which is a processor having a circuit configuration that is changeable after manufacture, and a dedicated electric circuit, such as an ASIC (application-specific integrated circuit), which is a processor having a circuit configuration specifically designed to perform specific processing.

One processing unit may be configured as one of the various processors or two or more processors of the same type or different types (for example, a plurality of FPGAs or a combination of a CPU and an FPGA). Further, a plurality of processing units may be configured as one processor. As the first example of configuring a plurality of processing units as one processor, a form is possible where one or more CPUs and software are combined to configure one processor, and the processor functions as the plurality of processing units, a representative example of which is a computer, such as a client or a server. As the second example thereof, a form is possible where a processor is used in which the functions of the entire system including the plurality of processing units are implemented as one IC (integrated circuit) chip, a representative example of which is a system on chip (SoC). As described above, regarding the hardware configuration, the various processing units are configured by using one or more of the various processors described above.

Further, the hardware configuration of the various processors is more specifically an electric circuit (circuitry) in which circuit elements, such as semiconductor elements, are combined.

The above-described configurations and functions can be implemented as any hardware, software, or a combination thereof as appropriate. For example, the present invention is applicable to a program that causes a computer to perform the above-described processing steps (processing procedure), a computer-readable recording medium (non-transitory recording medium) to which such a program is recorded, or a computer in which such a program can be installed.

Now, the display form of the display unit 111 is described. The display unit 111 displays at least the lesion count to assist the operator of an endoscopic examination.

Figure 7:
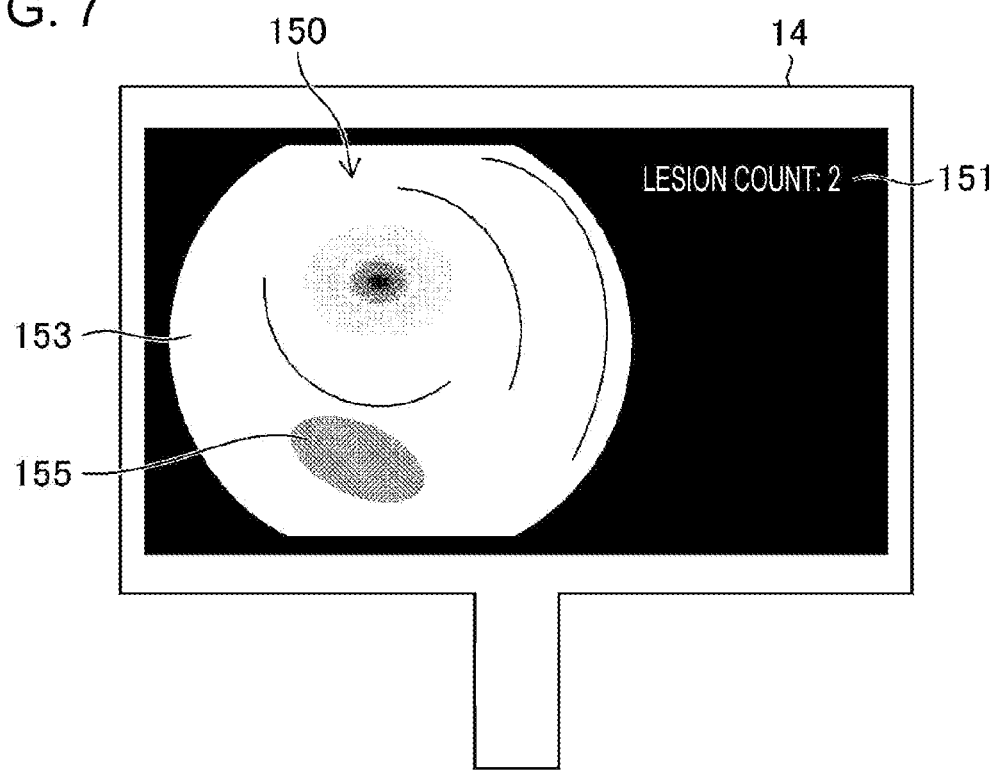
FIG. 7 illustrates example display by a display unit.
Figure 8:
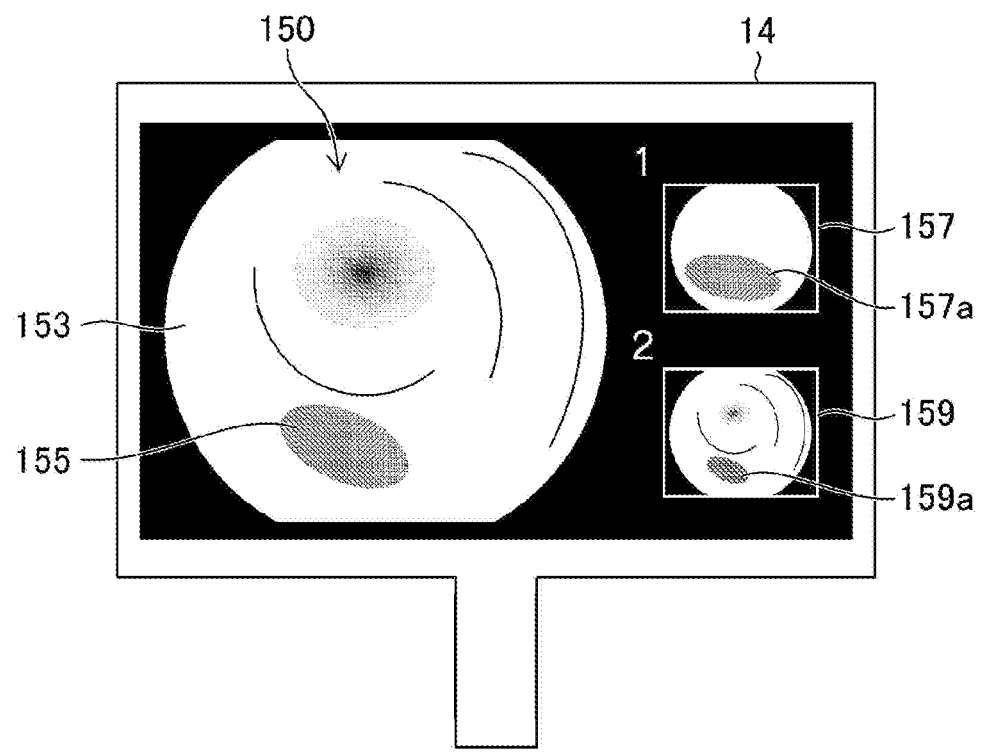
FIG. 8 illustrates example display by the display unit.

FIG. 7 and FIG. 8 are diagrams illustrating example display performed by the display unit 111.

FIG. 7 illustrates first example display by the display unit 111. In this example, a screen 150 showing an ongoing endoscopic examination is displayed on the display 14. On the screen 150 showing an ongoing endoscopic examination, an examination target 153 and a lesion 155 are displayed. In addition to the screen 150 showing the ongoing endoscopic examination, a lesion count 151, which is the number of found lesions, is displayed.

FIG. 8 illustrates second example display by the display unit 111. In this example, the screen 150 showing an ongoing endoscopic examination is displayed on the display 14. On the display 14, second lesion images 157 and 159, which are images of previously detected lesions, are displayed. Note that the second lesion images 157 and 159 are assigned numbers in accordance with the order in which the lesions were found (the second lesion image 157 is assigned the number "1" and the second lesion image 159 is assigned the number "2"). Here, the second lesion images 157 and 159 are representative images among the lesion images of a lesion 157a and a lesion 159a respectively.

As described above, the lesion count, which is the number of lesions detected in a single endoscopic examination, is counted, and the counted lesion count is displayed on the display unit 111. Therefore, the strain on the operator performing an endoscopic examination can be reduced, and the endoscopic examination can be performed accurately and efficiently.

Second Embodiment

Now, a second embodiment is described. In this embodiment, an endoscopic examination is divided into a first examination and a second examination, and the lesion count is counted in each of the first examination and the second examination.

Figure 9:
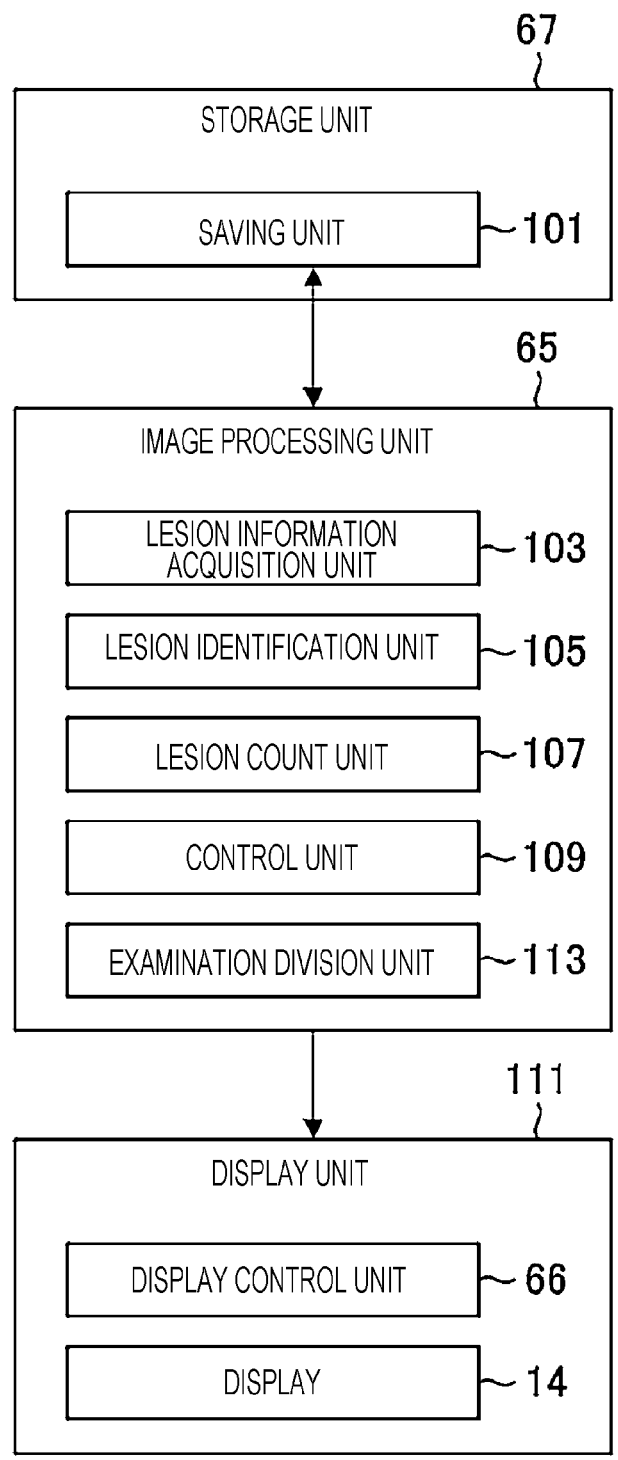
FIG. 9 is a block diagram illustrating an example major functional configuration of the endoscope apparatus.

FIG. 9 is a block diagram illustrating an example major functional configuration of the endoscope apparatus 10. The saving unit 101 is provided in the storage unit 67. The lesion information acquisition unit 103, the lesion identification unit 105, the lesion count unit 107, the control unit 109, and an examination division unit 113 are provided in the image processing unit 65. The display unit 111 is formed of the display control unit 66 and the display 14. A unit that has already described with reference to FIG. 3 is assigned the same reference numeral, and a description thereof is omitted.

The examination division unit 113 outputs to the control unit 109 a division instruction for dividing a single endoscopic examination into a first examination and a second examination. The control unit 109 causes the lesion count unit 107 to count the lesion count in the first examination and the lesion count in the second examination separately on the basis of the division instruction. There are a case where the examination division unit 113 outputs the division instruction to the control unit 109 on the basis of an instruction given by the operator (user) and a case where the examination division unit 113 automatically outputs the division instruction to the control unit 109.

In the case where the examination division unit 113 outputs the division instruction on the basis of an instruction given by the operator, for example, the operator inputs the division instruction to the examination division unit 113 via an input device, such as a button, of the handheld operation part 17. The operator may input the division instruction using a voice input device (not illustrated) provided in the endoscope apparatus 10.

In the case where the examination division unit 113 automatically outputs the division instruction, for example, the examination division unit 113 automatically recognizes a part that is the examination target from a captured image captured by the endoscope apparatus 10 and outputs the division instruction. For example, the examination division unit 113 outputs the division instruction at an examination time set in advance by the operator. For example, the examination division unit 113 recognizes the position of the scope and outputs the division instruction. For example, the examination division unit 113 recognizes the movement direction of the endoscope 11 and outputs the division instruction.

As a specific example of examination division, the first examination is an examination at the time when the scope is inserted, and the second examination is an examination at the time when the scope is withdrawn. In this case, the examination division unit 113 determines whether the direction in which the scope is currently moving is the insertion direction or the withdrawal direction and performs switching. The examination division unit 113 may recognize a halfway point and assume that an examination beyond the halfway point is the examination at the time of withdrawal. For example, in a case of the large intestine, a location that is recognized as the Bauhin's valve is assumed to be the halfway point. Note that acquired lesion information and existing lesion information in the period of the first examination are compared in the first examination, and acquired lesion information and existing lesion information in the period of the second examination are compared in the second examination.

Figure 10:
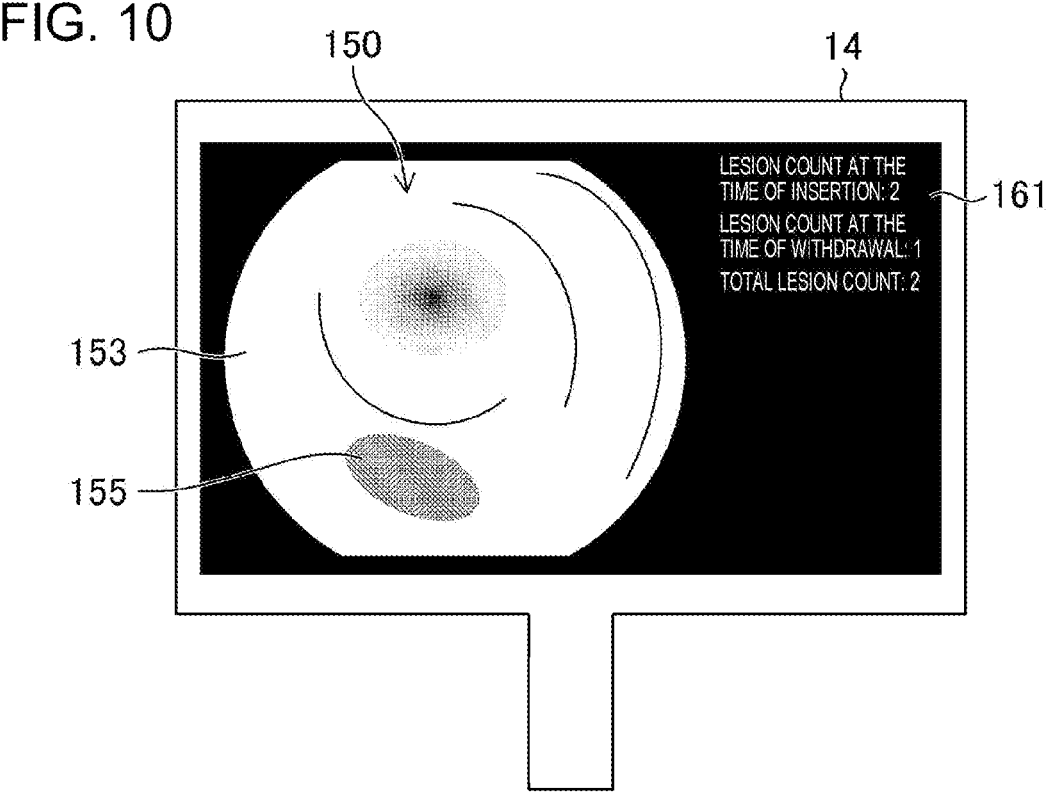
FIG. 10 illustrates example display by the display unit.
Figure 11:
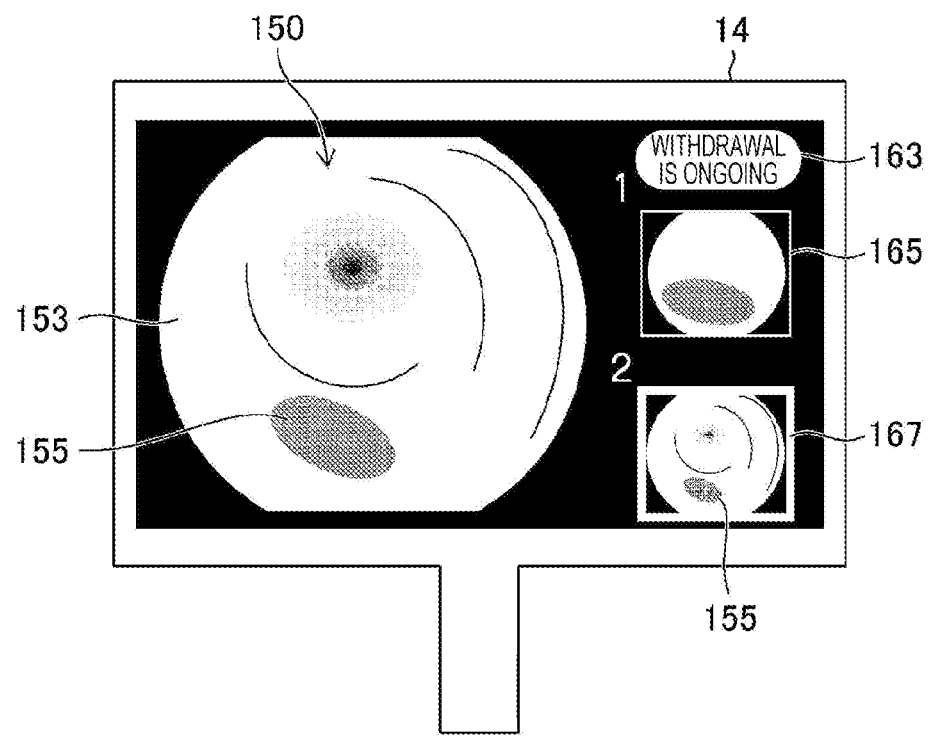
FIG. 11 illustrates example display by the display unit.

FIG. 10 and FIG. 11 are diagrams illustrating example display performed by the display unit 111 of the endoscope apparatus 10 according to this embodiment.

FIG. 10 illustrates third example display by the display unit 111. In this example, lesion counts 161 are displayed in addition to the screen 150 showing the ongoing endoscopic examination. As the lesion counts 161, the lesion count at the time of insertion, the lesion count at the time of withdrawal, and the total lesion count are displayed. At the time when the endoscope 11 is inserted, two lesions are found, and the total lesion count of "2" is displayed accordingly.

FIG. 11 illustrates fourth example display by the display unit 111. In this example, representative images of lesions found at the time of insertion are displayed in addition to the screen 150 showing the ongoing endoscopic examination. Specifically, the name of the currently performed examination ("withdrawal is ongoing") 163 is displayed, and a representative image 165 and a representative image 167 of lesions found at the time of insertion are displayed. In a case where a lesion found at the time of insertion is found again at the time of withdrawal, for example, the representative image is highlighted. In the case illustrated in FIG. 11, the lesion 155 is displayed on the screen 150 showing the ongoing endoscopic examination, and the same lesion 155 is also present in the representative image 167. Therefore, the representative image 167 is highlighted.

As described above, the examination division unit 113 outputs to the control unit 109 a division instruction for dividing an endoscopic examination into a first examination and a second examination, and the control unit 109 causes the lesion count unit 107 to count the lesion count in the first examination and the lesion count in the second examination separately on the basis of the division instruction. Accordingly, in a single endoscopic examination, the lesion count can be counted separately, and the operator can be assisted more appropriately.

Third Embodiment

Now, a third embodiment is described. In this embodiment, a remaining lesion count is displayed.

Figure 12:
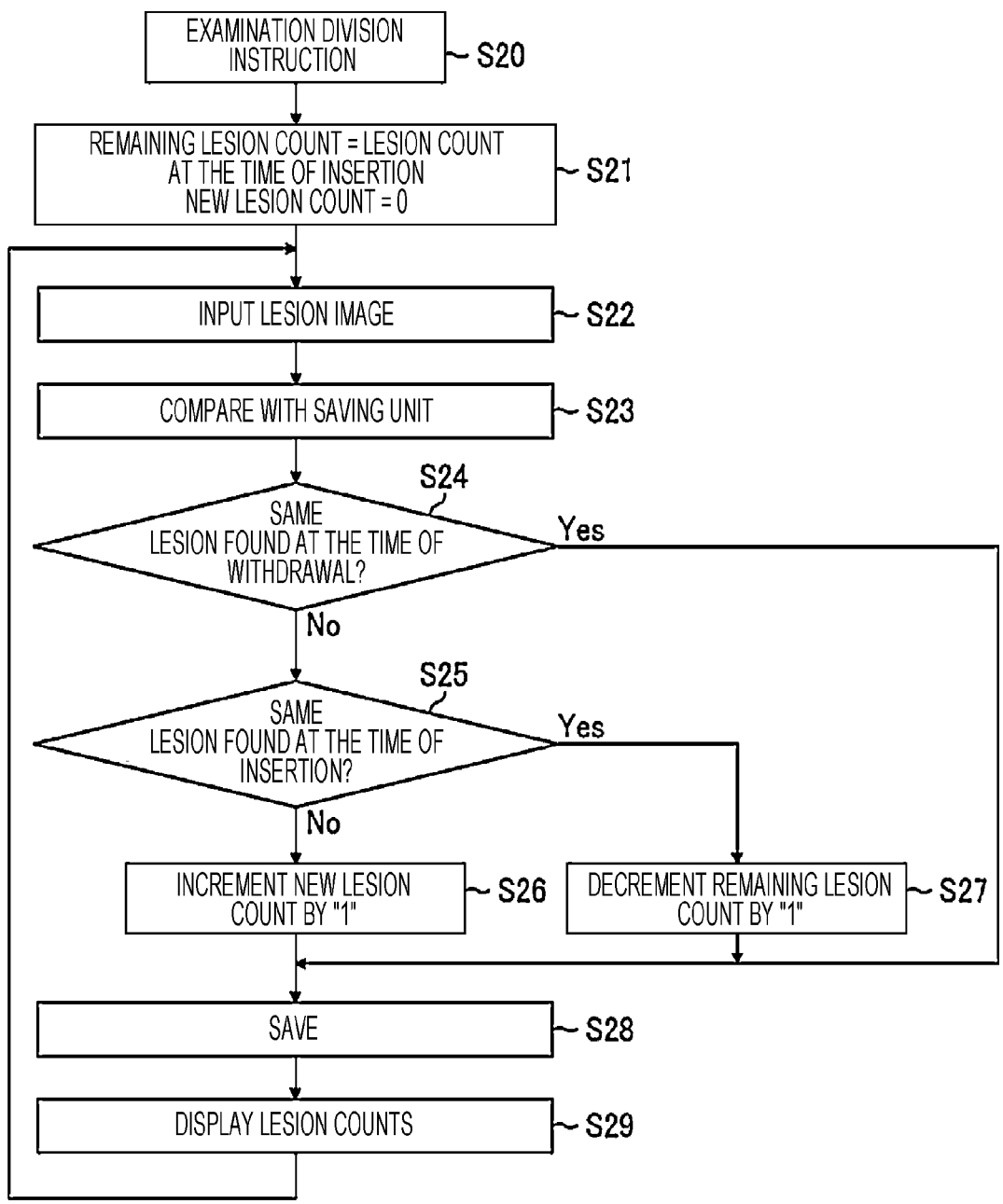
FIG. 12 is a flowchart illustrating operations by the endoscope apparatus.

FIG. 12 is a flowchart illustrating operations by the endoscope apparatus 10 according to this embodiment. The example illustrated in FIG. 12 is a case where an endoscopic examination is divided into an examination at the time of insertion of the endoscope 11 and an examination at the time of withdrawal of the endoscope 11. A case where a first lesion image and a second lesion image are input as acquired lesion information and existing lesion information respectively is described.

Insertion of the endoscope 11 is completed, an instruction is input from the operator via the handheld operation part 17, and the examination division unit 113 outputs a division instruction to the control unit 109 (step S20). Thereafter, the control unit 109 sets counts counted by the lesion count unit 107 such that a remaining lesion count=the lesion count at the time of insertion and a new lesion count=0 hold (step S21). Here, a remaining lesion count is the number of lesions found at the time of insertion (first examination). At the time of withdrawal, the control unit 109 causes the lesion count unit 107 to decrement the remaining lesion count by one to update the remaining lesion count. Next, at the time of withdrawal, a first lesion image, which is acquired lesion information, is input to the lesion information acquisition unit 103 (step S22).

Thereafter, the lesion identification unit 105 compares the input first lesion image with second lesion images saved in the saving unit 101 (step S23). First, the lesion identification unit 105 determines whether a second lesion image that represents the same lesion represented by the first lesion image and found at the time of withdrawal is present (step S24). In a case where the lesion identification unit 105 determines that a second lesion image that represents the same lesion represented by the first lesion image and found at the time of withdrawal is not present, the lesion identification unit 105 subsequently determines whether a second lesion image that represents the same lesion represented by the first lesion image and found at the time of insertion is present (step S25). In a case where the lesion identification unit 105 determines that the same lesion has been found at the time of insertion, the control unit 109 decrements the remaining lesion count retained by the lesion count unit 107 by one (step S27). On the other hand, in a case where the lesion identification unit 105 determines that the same lesion has not been found at the time of insertion, the control unit 109 increments the new lesion count retained by the lesion count unit 107 by one (step S26). Thereafter, the first lesion image is saved in the saving unit 101 as a second lesion image (step S28), and the display unit 111 displays the new lesion count and the remaining lesion count retained by the lesion count unit 107.

On the other hand, in a case where the lesion identification unit 105 determines that a second lesion image that represents the same lesion represented by the first lesion image and found at the time of withdrawal is present, the first lesion image is saved in the saving unit 101, and the remaining lesion count and the new lesion count retained by the lesion count unit 107 are maintained and displayed by the display unit 111 (step S29). As described above, in the case where an endoscopic examination is divided into a first examination and a second examination, the lesion identification unit 105 compares acquired lesion information and existing lesion information in the first examination and compares acquired lesion information and existing lesion information in the second examination.

Figure 13:
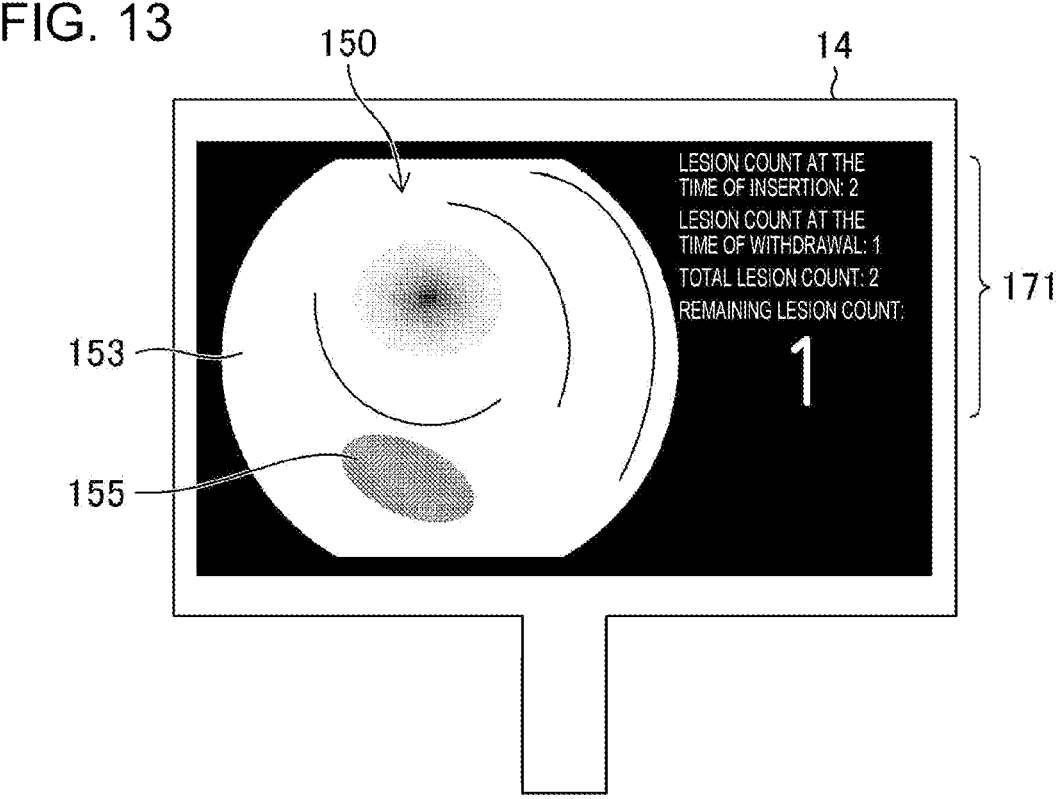
FIG. 13 illustrates example display by the display unit.
Figure 14:
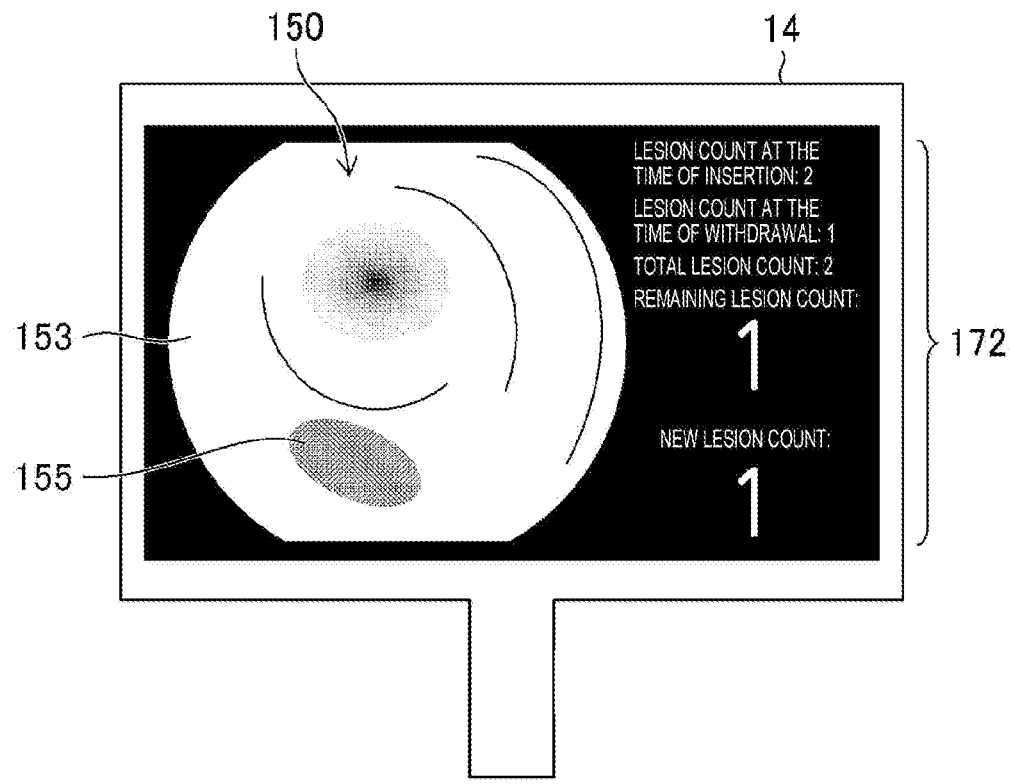
FIG. 14 illustrates example display by the display unit.

FIG. 13 and FIG. 14 are diagrams illustrating example display performed by the display unit 111 of the endoscope apparatus 10 according to this embodiment.

FIG. 13 illustrates fifth example display by the display unit 111. In this example, lesion counts 171 are displayed in addition to the screen 150 showing the ongoing endoscopic examination. As the lesion counts 171, the lesion count at the time of insertion, the lesion count at the time of withdrawal, the total lesion count, and the remaining lesion count are displayed.

FIG. 14 illustrates sixth example display by the display unit 111. In this example, lesion counts 172 are displayed in addition to the screen 150 showing the ongoing endoscopic examination. As the lesion counts 172, the lesion count at the time of insertion, the lesion count at the time of withdrawal, the total lesion count, the remaining lesion count, and the new lesion count are displayed.

As described above, the remaining lesion count is updated, and the remaining lesion count is displayed on the display unit 111, and therefore, the operator can be assisted appropriately in performing an examination. For example, the operator performs an endoscopic examination while checking the remaining lesion count, which can reduce the possibility of overlooking a lesion at the time of the endoscopic examination.

Examples of the present invention have been described above; however, the present invention is not limited to the above-described embodiments, and various modifications can be made without departing from the spirit of the present invention as a matter of course.

REFERENCE SIGNS LIST

10 endoscope apparatus
11 endoscope
12 light source device
12a light source operation part
13 processor device
13a processor operation part
14 display
16 insertion part
16a insertion part tip part
16b bending part
16c flexible pipe part
17 handheld operation part
18 universal cord
21 angle knob
22 operation button
23 forceps port
25a connector part
25b connector part
31 light source control unit
32 light source unit
32a V-LED
32b B-LED
32c G-LED
32d R-LED
40 light guide
42 illumination lens
44 object lens
45 imaging device
47 endoscope control unit
48 ROM
61 processor control unit
62 ROM
65 image processing unit
66 display control unit
67 storage unit
101 saving unit
102 lesion detection unit
103 lesion information acquisition unit
105 lesion identification unit
107 lesion count unit
109 control unit
111 display unit
113 examination division unit
150 screen

What is claimed is:

1. An endoscope apparatus comprising:
a display; and
one or more processors, configured to:
acquire, in a case where a lesion is detected from time-series images captured during an endoscopic examination period, acquired lesion information that indicates at least one of a first lesion image representing the detected lesion or a feature value indicating a feature of the first lesion image;
compare an existing feature value indicating a feature of a second lesion image in existing lesion information, which is the acquired lesion information previously, with the feature value that indicates the feature of the first lesion image in a newly acquired lesion information and determine whether the newly acquired lesion information indicates the same lesion indicated by the existing lesion information on basis of whether a similarity between the existing feature value and the feature value is equal to or higher than a threshold value;
count a lesion count, which is the number of lesions detected in a single endoscopic examination;
control the display to display the lesion count; and
increment the lesion count by one when the one or more processors determines that the newly acquired lesion information does not indicate the same lesion indicated by the existing lesion information.

2. The endoscope apparatus according to claim 1, wherein the one or more processors is further configured to:

output a division instruction for dividing the endoscopic examination into a first examination and a second examination; and count a lesion count in the first examination and a lesion count in the second examination separately on the basis of the division instruction.

3. The endoscope apparatus according to claim 2, wherein in the division instruction, the first examination is an examination that is performed at the time of insertion of a scope, and the second examination is an examination that is performed at the time of withdrawal of the scope.

4. The endoscope apparatus according to claim 3, wherein the one or more processors is configured to display the lesion count together with an image showing the endoscopic examination that is ongoing.

5. The endoscope apparatus according to claim 2, wherein the one or more processors is configured to output the division instruction on the basis of a user instruction.

6. The endoscope apparatus according to claim 5, wherein the one or more processors is configured to display the lesion count together with an image showing the endoscopic examination that is ongoing.

7. The endoscope apparatus according to claim 2, wherein the one or more processors is configured to automatically output the division instruction.

8. The endoscope apparatus according to claim 7, wherein the one or more processors is configured to display the lesion count together with an image showing the endoscopic examination that is ongoing.

9. The endoscope apparatus according to claim 2, wherein the one or more processors is configured to display the lesion count together with an image showing the endoscopic examination that is ongoing.

10. The endoscope apparatus according to claim 2, wherein the one or more processors is configured to display the lesion count in the first examination and the lesion count in the second examination.

11. The endoscope apparatus according to claim 1, wherein the one or more processors is configured to display the lesion count together with an image showing the endoscopic examination that is ongoing.

12. The endoscope apparatus according to claim 1, wherein the existing lesion information has the second lesion image corresponding to the first lesion image, and the one or more processors is configured to display the lesion count together with the second lesion image.

13. The endoscope apparatus according to claim 1, wherein the one or more processors is further configured to save the existing lesion information, compare the existing lesion information saved with the acquired lesion information newly and determine whether the newly acquired lesion information indicates the same lesion indicated by the existing lesion information.

14. The endoscope apparatus according to claim 13, wherein the one or more processors is configured to save all or some of pieces of acquired lesion information acquired as pieces of existing lesion information.

15. An endoscope apparatus comprising one or more processors, configured to:

acquire, in a case where a lesion is detected from time-series images captured during an endoscopic examination period, acquired lesion information that indicates at least one of a first lesion image representing the detected lesion or a feature value indicating a feature of the first lesion image;

identify a lesion from the time-series images;

count a lesion count, which is the number of lesions detected in a single endoscopic examination;

display the lesion count counted;

output a division instruction for dividing the endoscopic examination into a first examination that is performed at the time of insertion of a scope and a second examination that is performed at the time of withdrawal of the scope;

in the first examination, compare existing lesion information, which is the acquired lesion information previously, with the a newly acquired lesion information and determine whether the newly acquired lesion information indicates the same lesion indicated by the existing lesion information, and increment the lesion count counted by one when the one or more processors determines that the newly acquired lesion information does not indicate the same lesion indicated by the existing lesion information, and in the second examination that follows the first examination, compare the existing lesion information previously acquired in the first examination with the acquired lesion information newly acquired in the second examination and determine whether the newly acquired lesion information indicates the same lesion indicated by the existing lesion information previously acquired in the first examination, decrement a remaining lesion count by one to update the remaining lesion count, the remaining lesion count being the lesion count when the first examination is completed, in a case where the one or more processors determines that the newly acquired lesion information indicates the same lesion indicated by the existing lesion information previously acquired in the first examination, and display the remaining lesion count on the basis of the remaining lesion count.

16. The endoscope apparatus according to claim 15, wherein in a case where the one or more processors determines that the newly acquired lesion information does not indicate the same lesion indicated by the existing lesion information in the first examination, the one or more processors do a count as a new lesion count in the second examination, and display the new lesion count.

17. The endoscope apparatus according to claim 16, wherein the one or more processors is configured to display the lesion count together with an image showing the endoscopic examination that is ongoing.

18. The endoscope apparatus according to claim 15, wherein the one or more processors is configured to display the lesion count together with an image showing the endoscopic examination that is ongoing.

19. An endoscope operation method comprising:

acquiring, in a case where a lesion is detected from time-series images captured during an endoscopic examination period, acquired lesion information that indicates at least one of a first lesion image representing the detected lesion or a feature value indicating a feature of the first lesion image;

comparing an existing feature value indicating a feature of a second lesion image in existing lesion information, which is the acquired lesion information previously, with the feature value that indicates the feature of the first lesion image in a newly acquired lesion information and determining whether the newly acquired lesion information indicates the same lesion indicated by the existing lesion information on basis of whether a similarity between the existing feature value and the feature value is equal to or higher than a threshold value;

counting a lesion count, which is the number of lesions detected in a single endoscopic examination;

controlling to display the lesion count; and incrementing the lesion count by one when determining that the newly acquired lesion information does not indicate the same lesion indicated by the existing lesion information.

20. A non-transitory computer readable recording medium storing a program causing a computer to perform an endoscope operation process comprising:

acquiring, in a case where a lesion is detected from time-series images captured during an endoscopic examination period, acquired lesion information that indicates at least one of a first lesion image representing the detected lesion or a feature value indicating a feature of the first lesion image;

comparing an existing feature value indicating a feature of a second lesion image in existing lesion information, which is the acquired lesion information previously, with the feature value that indicates the feature of the first lesion image in a newly acquired lesion information and determining whether the newly acquired lesion information indicates the same lesion indicated by the existing lesion information on basis of whether a similarity between the existing feature value and the feature value is equal to or higher than a threshold value;

counting a lesion count, which is the number of lesions detected in a single endoscopic examination;

controlling to display the lesion count; and incrementing the lesion count by one when determining that the newly acquired lesion information does not correspond to the same lesion indicated by the existing lesion information.

\* \* \* \* \*